United States Patent
Sugiyama et al.

(10) Patent No.: US 6,251,618 B1
(45) Date of Patent: *Jun. 26, 2001

(54) COLOR DEVELOPING METHOD, ENZYME IMMUNOASSAY USING THE COLOR DEVELOPING METHOD, AND IMMUNOCHROMATOGRAPHY INCORPORATING THE ENZYME IMMUNOASSAY

(75) Inventors: Masami Sugiyama; Mamoru Miyazaki; Yoshihiro Ashihara, all of Tokyo (JP)

(73) Assignee: Fujirebio Inc., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/417,220

(22) Filed: Oct. 13, 1999

Related U.S. Application Data

(63) Continuation of application No. 09/104,166, filed on Jun. 25, 1998, now Pat. No. 5,998,156.

(30) Foreign Application Priority Data

Jun. 25, 1997 (JP) .................................................. 9-183248

(51) Int. Cl.$^7$ ....................... G01N 33/543; G01N 33/576
(52) U.S. Cl. ............................. 435/7.92; 435/5; 435/7.94; 435/18; 435/21; 435/962
(58) Field of Search ............................. 435/7.92, 12, 21, 435/18, 5, 962, 7.94

(56) References Cited

U.S. PATENT DOCUMENTS

| 5,089,391 | * | 2/1992 | Buechler et al. | 435/7.1 |
| 5,370,994 | * | 12/1994 | Stewart et al. | 435/12 |
| 5,683,988 | * | 11/1997 | Chung | 514/44 |
| 5,807,993 | * | 9/1998 | French et al. | 530/350 |

* cited by examiner

Primary Examiner—Mary E. Ceperley
(74) Attorney, Agent, or Firm—Oblon, Spivak, McClelland, Maier & Neustadt, P.C.

(57) ABSTRACT

Disclosed are a color developing method utilizing the reaction of an indolyl derivative with an enzyme in the presence of a specific free radical compound and/or a specific chelate compound, and an enzyme immunoassay using the color developing method.

7 Claims, 1 Drawing Sheet

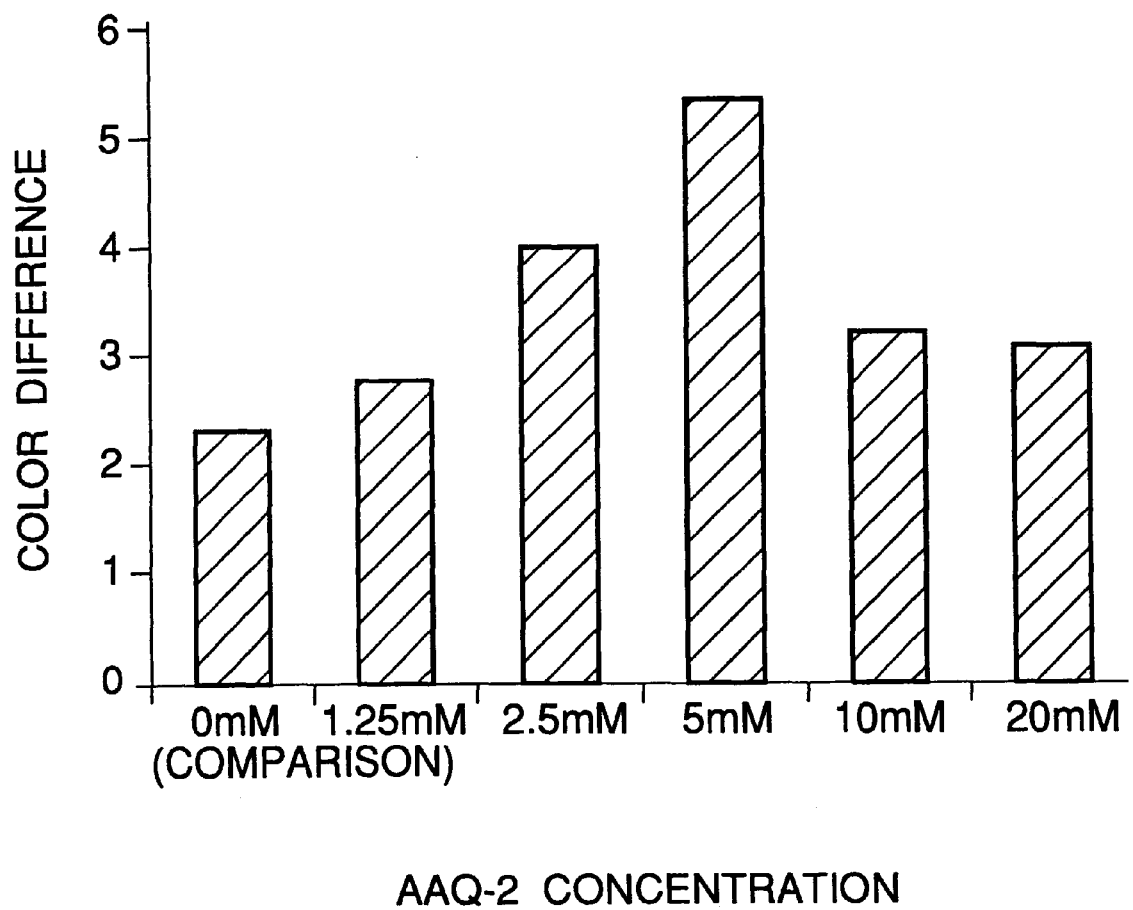
FIGURE

COLOR DEVELOPING METHOD, ENZYME IMMUNOASSAY USING THE COLOR DEVELOPING METHOD, AND IMMUNOCHROMATOGRAPHY INCORPORATING THE ENZYME IMMUNOASSAY

This application is a continuation of application Ser. No. 09/104,166 filed on Jun. 25, 1998, now U.S. Pat. No. 5,998,156.

FIELD OF THE INVENTION

This invention relates to a method of color development using the reaction of an indolyl derivative as a color developing substrate with an enzyme in the presence of a free radical compound and/or a chelate compound, an enzyme immunoassay (hereinafter abbreviated as EIA) utilizing the method of color development, and an immunochromatography incorporating the enzyme immunoassay.

BACKGROUND OF THE INVENTION

An indolyl derivative has been used as a color developing substrate in immunoblotting or immunochromatography (see Methods in Enzymology, Vol. 121, pp. 497–509 (1986) and JP-A-9-133681 which corresponds to EP-A-0762123, the term "JP-A" as used herein means an "unexamined published Japanese patent application"). In these techniques, the activity of an enzyme immobilized on a nitrocellulose membrane through immune reaction is determined by the use of an indolyl derivative. The indolyl derivative reacts with the immobilized enzyme to form an indigoid dye, which is deposited on the membrane with the passage of time to visualize the reaction product.

Immunoblotting requires 20 to 60 minutes from the start of the reaction between an indolyl derivative and an enzyme to color detection, and it has been desired to shorten the reaction time. In immunochromatography, it takes at least 10 minutes, usually from 15 minutes to several hours, for dot blotting a membrane with a sample, development with a developing solution containing an indolyl derivative, and measuring the color developed at the detecting portion to obtain a result. In order to take full advantage of the simplicity characteristic of immunochromatography in urgent examination, it has also been desired to further shorten the time of assaying.

SUMMARY OF THE INVENTION

A first object of the present invention is to provide an improved color developing method using the reaction of an indolyl derivative with an enzyme in the presence of a free radical compound and/or a chelate compound.

A second object of the present invention is to provide an enzyme immunoassay utilizing the above color developing method.

A third object of the present invention is to provide an immunochromatography incorporating the above enzyme immunoassay.

As a result of extensive studies to achieve the above-described objects, the present inventors have found that the time required for color development can be reduced by the reaction of an indolyl derivative with an enzyme in the presence of a specific free radical compound and/or a specific chelate compound.

That is, the present invention provides a color developing method comprising reacting an indolyl derivative represented by formula (I):

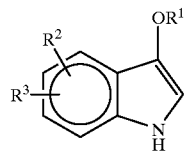

(I)

wherein $R^1$ represents an enzymatically releasable group; and $R^2$ and $R^3$ each represents a hydrogen atom or a halogen atom, and an enzyme in the presence of a free radical compound represented by formula (II):

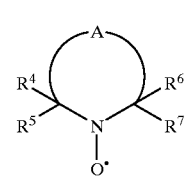

(II)

wherein A represents a substituted or unsubstituted methylene chain having 2 or 3 carbon atoms which may contain in its chain an oxygen atom or a carbonyl group; and $R^4$, $R^5$, $R^6$, and $R^7$ each represent a hydrogen atom or an alkyl group having 1 to 3 carbon atoms, and/or a chelate compound formed between a diamine derivative represented by formula (III):

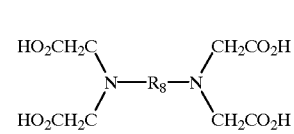

(III)

wherein $R^8$ represents an ethylene group or a cyclohexane-1,2-diyl group, and a metal selected from the group consisting of iron, copper, zinc, cobalt, indium, neodymium, manganese and europium.

The present invention also provides an enzyme immunoassay comprising measuring enzyme activity of an enzyme-labelled antibody or antigen by using the reaction of the indolyl derivative represented by formula (I) with an enzyme, wherein said reaction is carried out in the presence of the free radical compound represented by formula (II) and/or the chelate compound formed between the diamine derivative represented by formula (III) and a metal selected from the group consisting of iron, copper, zinc, cobalt, indium, neodymium, manganese and europium.

The present invention further provides an immunochromatography comprising measuring enzyme activity of an enzyme-labelled antibody or antigen which is bound to a detecting portion on a solid phase by using the reaction of the indolyl derivative represented by formula (I) with an enzyme, wherein said reaction is carried out in the presence of the free radical compound represented by formula (II) and/or the chelate compound formed between the diamine derivative represented by formula (III) and a metal selected from the group consisting of iron, copper, zinc, cobalt, indium, neodymium, manganese and europium.

BRIEF DESCRIPTION OF THE DRAWING

FIG. 1 is a graph of color intensity developed at a varied AAQ-2 concentration.

DETAILED DESCRIPTION OF THE INVENTION

The color developing method according to the present invention is characterized in that the free radical compound of formula (II) and/or the chelate compound are present in the color developing system in which the releasable group $R^1$ of the indolyl derivative of formula (I) is released by the action of an enzyme and two molecules of the residue are condensed to form an indigoid dye. After a prescribed reaction time, the produced indigoid dye can be detected with the naked eye or by means of instruments.

The free radical compound and/or the chelate compound can be added to the reaction solution containing the indolyl derivative, usually a buffer solution containing the indolyl derivative, to a total concentration of from preferably about 0.1 to 100 mM, more preferably about 1 to 20 mM. The reaction is preferably carried out in a buffer. Examples of suitable buffers include a diethanolamine-HCl buffer, an aminomethylpropanediol-HCl buffer, a carbonate buffer, a glycine buffer, a CHES-NaOH buffer (CHES: N-cyclohexyl-2-aminoethanesulfonic acid), a CAPSO-NaOH buffer (CAPSO: N-cyclohexyl-2-hydroxy-3-aminopropanesulfonic acid), and a CAPS-NaOH buffer (CAPS: N-cyclohexyl-3-aminopropanesulfonic acid). If desired, salts such as magnesium chloride can be added to the buffer.

The free radical compound of formula (II) which can be used in the present invention is a cyclic amine compound having an N-oxyl free radical. In formula (II), A is a substituted or unsubstituted methylene chain having 2 or 3 carbon atoms. The methylene chain can contain in its chain an oxygen atom or a carbonyl group. Examples of A include $—(CH_2)_3—$, $—(CH_2)_2—$, $—CH_2—O—CH_2—$, and $—CH_2—CO—CH_2—$. Substituents on the methylene chain include a hydroxyl group, a carboxyl group, a carbamoyl group (e.g., carbamoyl, methylcarbamoyl, ethylcarbamoyl, propylcarbamoyl or phenylcarbamoyl), and an amino group. $R^4$, $R^5$, $R^6$, and $R^7$, which may be the same or different, each represents a hydrogen atom or an alkyl group having 1 to 3 carbon atoms, such as methyl, ethyl, n-propyl or isopropyl. Preferably at least one of $R^4$ to $R^8$ represents an alkyl group having 1 to 3 carbon atoms, and more preferably $R^4$ to $R^3$ each represents an alkyl group having 1 to 3 carbon atoms. Where the carbon atom adjacent to the ring-forming nitrogen atom is substituted with an alkyl group, the free radical is stabilized.

The free radical compound of formula (II) are easily available and includes N-oxyl-2,2,6,6-tetramethylpiperidine, N-oxyl-4-hydroxy-2,2,6,6-tetramethylpiperidine, N-oxyl-4-carboxy-2,2,6,6-tetramethylpiperidine, N-oxyl-4-carbamoyl-2,2,6,6-tetramethylpiperidine, N-oxyl-4-amino-2,2,6,6-tetramethylpiperidine, N-oxyl-2,2,6,6-tetramethylmorpholine, N-oxyl-2,2,5,5-tetramethylpyrrolidine, N-oxyl-3-hydroxy-2,2,5,5-tetramethylpyrrolidine, N-oxyl-3-carboxyl-2,2,5,5-tetramethylpyrrolidine, N-oxyl-3-carbamoyl-2,2,5,5-tetramethylpyrrolidine, and N-oxyl-4-oxo-2,2,6,6-tetramethylpiperidine (AAQ-2).

In formula (III), $R^8$ includes an ethylene group and a cyclohexane-1,2-diyl group.

The chelate compound which can be used in the present invention include complexes in which ethylenediaminetetraacetic acid (EDTA), trans-1,2-diaminecyclohexane-N,N,N',N'-tetraacetic acid, etc. are coordinating to a center metal, such as iron, copper, zinc, cobalt, indium, neodymium, manganese, and europium. Specific examples of the chelate compounds are EDTA-iron, EDTA-copper, EDTA-zinc, EDTA-cobalt, EDTA-indium, EDTA-manganese, EDTA-europium, trans-1,2-diaminecyclohexane-N,N,N',N'-tetraacetic acid-iron, and trans-1,2-diaminecyclohexane-N,N,N', N'-tetraacetic acid-copper.

In formula (I) representing the indolyl derivative used as a substrate, $R^1$ is a releasable group that is decomposed and released by the action of an enzyme. Examples of such an enzymatically releasable group include a group represented by $—PO_3^{2-}·2M^+$ (wherein M is a hydrogen atom, an alkali metal or toluidine), a β-D-galactopyranosyl group, and a β-D-glucopyranosyl group.

The indolyl derivative used as a substrate for a phosphatase is represented by formula (Ia):

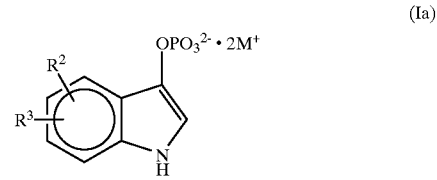

wherein $R^2$, $R^3$, and M are as defined above;
the one for β-D-galactosidase is represented by formula (Ib):

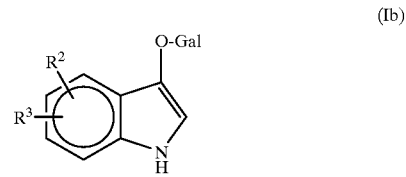

wherein $R^2$ and $R^3$ are as defined above; and Gal represents a β-D-galactopyranosyl group; and the one for β-D-glucosidase is represented by formula (Ic):

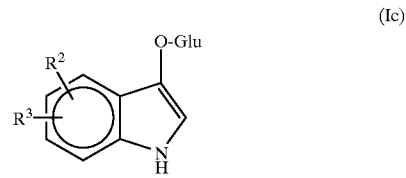

wherein $R^2$ and $R^3$ are as defined above; and Glu represents a β-D-glucopyranosyl group.

The halogen atom represented by $R^2$ and $R^3$ includes chlorine, bromine, and iodine. It is preferred for the halogen atom as $R^2$ or $R^3$ to be bonded to the 4- or 5-position of the indoline skeleton.

The alkali metal in the indolyl derivative of formula (Ia) includes sodium and potassium. Specific examples of the indolyl derivatives of formula (Ia) are 3-indolylphosphoric acid, 5-bromo-4-chloro-3-indolylphosphoric acid, 5-bromo-6-chloro-3-indolylphosphoric acid, disodium 3-indolylphosphate, disodium 5-bromo-4-chloro-3-indolylphosphate, disodium 5-bromo-6-chloro-3-indolylphosphate, p-toluidine 5-bromo-4-chloro-3-indolylphosphate, and p-toluidine 5-bromo-6-chloro-3-indolylphosphate.

Specific examples of the indolyl derivative of formula (Ib) are 3-indolyl-β-D-galactopyranoside, 5-bromo-4-chloro-3-indolyl-β-D-galactopyranoside, and 5-bromo-6-chloro-3-indolyl-β-D-galactopyranoside.

Specific examples of the indolyl derivative of formula (Ic) are 3-indolyl-β-D-glucopyranoside, 5-bromo- 4-chloro-3-indolyl-β-D-glucopyranoside, and 5-bromo-6-chloro-3-indolyl-β-D-glucopyranoside.

The color developing method of the present invention can be taken advantage of in EIA using an enzyme-labelled reagent, immunoblotting, phosphatase isozyme analysis by electrophoresis, tissue staining, and genetic analysis on DNA or RNA using an enzyme as a labelled substance.

EIA can be carried out with a kit comprising an appropriate combination of an enzyme-labelled reagent (an antigen or antibody labelled with the above-mentioned enzyme) and a solid phase reagent (an antigen or antibody immobilized on a carrier) in a usual manner. The enzyme-labelled reagent can be prepared by linking the enzyme to an antigen or an antibody through covalent bonding or non-covalent bonding. Methods for linking by covalent bonding include a glutaraldehyde method, a periodic acid method, a meleimide method, a pyridyl-disulfide method, and a method using various known crosslinking agents (e.g., a maleimide reagent) (see *Protein Nucleic Acid and Enzyme*, Special Ed., No. 31, pp. 37–45 (1987)). Linking by non-covalent bonding can be effected by physical adsorption of the enzyme onto an antibody or an antigen.

The solid phase reagent is prepared by binding an antibody or an antigen to a solid carrier customarily used in various EIA techniques. Useful solid carriers include a plastic test tube, a plastic microtiter plate, latex particles (e.g., polystyrene), glass beads, plastic beads, a membrane of cellulose, nitrocellulose, etc., and magnetic particles. The solid phase reagent can be prepared by reacting with an antigen or an antibody by making use of the above-described covalent or non-covalent bonding methods.

While in the above description on EIA an antibody or an antigen has been referred to as an immune reactant that is to be labelled with an enzyme or immobilized on a solid carrier, the terminology "antibody" or "antigen" as used herein is intended to include substances capable of antigen-antibody reaction to form an immune complex, such as a polyclonal antibody, a monoclonal antibody, fragments of these antibodies (e.g., Fab, Fab', F(ab')$_2$), an d a hapten.

EIA using the above-mentioned solid phase reagent and enzyme-labelled reagent can be carried out by causing antigen-antibody reaction according to noncompetitive binding assay called a sandwich technique (including one-step technique, delayed one-step technique, and 2-step technique), a competitive binding assay, etc. or a combination thereof and determining the activity of either the enzyme of bound form or the enzyme of free form.

The EIA utilizing the color developing method of the present invention is applicable to immunochromatography using, for example, a membrane as a solid phase. In this case, the time for color developing reaction between the enzyme bound to a detection site and the indolyl derivative of formula (I) can be shortened so that the substance under assay can be determined in a short time however small its amount may be. The free radical compound and/or the chelate compound can be added to the membrane or a developing solution. Since the indolyl derivative of formula (I) used as a substrate produces a water-insoluble indigoid dye as a result of enzymatic reaction, the color developing method is suitably applied to immunochromatography and immunoblotting using a membrane. Measurement of the dye thus produced after a prescribed reaction time can be made by comparison with a standard color chart with the naked eye or, for more accuracy, by means of instruments, such as a color-difference meter, a calorimeter, an absorption spectrometer, and the like.

Particularly, in immunochromatography using a membrane, the dye to be produced by reaction between the enzyme and the indolyl derivative of formula (I) is preferably water-insoluble indigoid dye.

Substances which can be assayed by EIA according to the present invention include substances present in a living body, drugs, and the like. Examples of the substances include drugs, such as Theophylline, Phenytoin, and Valproic Acid; low-molecular hormones, such as thyroxine, estrogen, and estradiol; tumor markers, such as carcinoembryonic antigen (CEA), a-fetoproteins (AFP), and hemoglobin in the feces (FOBT: Fecal Occult Blood Test); viruses, such as human immunodeficiency virus (HIV), human T-cell leukemia virus (HTLV), hepatitis B virus (HBV), and hepatitis C virus (HCV); protozoa, such as *Treponema pallidum*; high-molecular hormones, such as thyroid-stimulating hormone (TSH) and insulin; cytokines, such as IL-1, IL-2 and IL-6; growth factors, such as epiderman growth factor (EGF) and platelet-derived growth factor (PDGF); and DNA, RNA, etc. of the above-described viruses; inflammation-related proteins, such as C-reactive protein (CRP); and antibodies against these antigens. Specimens to be assayed include body fluids, such as whole blood, serum, plasma, urine, and lympha; and a feces extract.

The present invention will now be illustrated in greater detail with reference to Reference Examples and Examples.

REFERENCE EXAMPLE 1

Preparation of Alkaline Phosphatase-labelled TP17 Antigen

To 0.12 mg of recombinant TP17 antigen was added 100 nmol of 2-iminothiorane. The system was allowed to stand at 30° C. for 30 minutes to introduce a thiol group to the antigen. To 3 mg of alkaline phosphatase was added 300 nmol of N-succinimidyl-4-maleimide butyrate (GMBS, produced by Dojindo Laboratories), followed by allowing to stand at 30° C. for 60 minutes to introduce a maleimide group into the enzyme. Then, 100 μg of the thiol-containing TP17 antigen and 2.5 mg of the maleimide-containing alkaline phosphatase were mixed to cause coupling reaction at 4° C. for one day. The reaction product was purified by gel filtration, and the fraction exhibiting the activity of the labelled enzyme was collected to obtain an alkaline phosphatase-labelled recombinant TP17 antigen (hereinafter referred to as alkaline phosphatase-labelled TP17 antigen).

Confirmation of the alkaline phosphatase-labelled TP17 antigen activity of each fraction was made as follows. A 5 mm wide and 30 mm long nitrocellulose membrane (produced by Millipore Corp.) was dotted 15 mm below the upper end with 3 μl of a recombinant TP17 antigen and dried at 37° C. for 30 minutes to prepare a test strip. Filter paper of 10 mm in width, 15 mm in length and 1 mm in thickness (Whatman WF1.5, produced by Whatman Ltd.) was fixed to the upper end of the test strip with a 5 mm overlap. A 25 μl aliquot of each fraction obtained by gel filtration and 25 μl of anti-TP antibody positive serum were mixed together in a test tube, and the lower end of the TP17 antigen-dotted test strip was dipped in the mixture for 5 minutes. The test strip was transferred into a test tube containing 250 μl of a 0.05% solution of 5-bromo-4-chloro-3-indolylphosphoric acid (hereinafter abbreviated as BCIP, available from Boehringer Mannheim Biochemica) and allowed to stand for 10 minutes. Where the fraction contained the alkaline phosphatase-labelled TP17 antigen, the antigen dotted portion developed a blue color.

EXAMPLE 1

Preparation of Test Strip for Assaying Anti-TP17 Antibody

A recombinant TP17 antigen was dotted to a 5 mm wide and 50 mm long nitrocellulose membrane (produced by Millipore Corp.) in a line 15 mm below the upper end by means of an applicator (Shot Master, produced by Musashi Engineering Co., Ltd.) and dried to fix the antigen (detection area). Filter paper of 10 mm in width and 20 mm in length (WF Wine Filter 1.5, produced by Whatman Ltd.) was fixed as an absorbent pad to the upper end of the membrane with a 5 mm overlap. A PVA sheet ("BELL-ETA", produced by Kanebo,.Ltd.) cut to a width of 5 mm and a length of 5 mm was dotted with 20 μl of the alkaline phosphatase-labelled TP17 antigen solution prepared in Reference Example 1 and dried, and the resulting sheet (labelled substance pad) was put on the membrane 25 mm below the upper end of the membrane. This sheet serves as a portion to which a specimen is dotted.

Filter paper of 5 mm in width and 20 mm in length (AP25, produced by Millipore Corp.) was fixed to the lower end of the nitrocellulose membrane with a 10 mm overlap to provide a substrate pad for dotting and development of a substrate solution. The substrate pad was dotted with 5 μl of a 20 mg/ml BCIP solution. The substrate pad was further dotted with 10 μl of 50 mM EDTA-Cu, 5 μl of 100 mM EDTA-Fe, 10 μl of 50 mM EDTA-Co or 10 μl of 50 mM EDTA-Nd. Thus, a test strip for assaying an anti-TP17 antibody was prepared.

For control, a test strip having no chelate compound in its substrate pad was prepared.

EXAMPLE 2

Assay of Anti-TP17 Antibody

The labelled substance pad of the test strip prepared in Example 1 was dotted with 15 μl of an anti-TP antibody specimen (TPPA titer: 20, 40 or 80), and 200 μl of a HES buffer (pH 10.5, containing 1 mM magnesium chloride) was then dropped on the substrate pad, absorbed, and spread to start reaction. The time for detecting positivity with the naked eye was recorded. The results are shown in Table 1 below.

TABLE 1

| TPPA Titer of Specimen | Average Detecting Time (sec) | | | | |
|---|---|---|---|---|---|
| | Chelate Compound | | | | |
| | EDTA-Cu | EDTA-Fe | EDTA-Co | EDTA-Nd | Control |
| 20 | 510 | 492 | 508 | 592 | 660 |
| 40 | 480 | 471 | 482 | 540 | 648 |
| 80 | 466 | 431 | 422 | 520 | 570 |

REFERENCE EXAMPLE 2

Preparation of Alkaline Phosphatase-Labelled Antibody

In 4 ml of a phosphate buffer (50 mM, pH 4.7) was d 30 mg of an anti-rabbit IgG antibody, and a 30 mg/ml solution of p-quinone in ethyl alcohol was added thereto, and the mixture was allowed to react at room temperature for 2 hours in a dark room. After the reaction, the buffer of the reaction solution was displaced with PD-10 (produced by Pharmacia) equilibrated with 150 mM sodium chloride. To the resulting IgG/p-quinone adduct solution was added 30 mg of alkaline phosphatase (available from Oriental; 2500 IU/mg), and the system was allowed to react in a refrigerator (4–10° C.) for 18 hours. After completion of the reaction, the product was purified with Superdex-100 (produced by Pharmacia) to obtain an alkaline phosphatase-labelled antibody.

EXAMPLE 3

Measurement of Color Developing Time in the Presence of Chelate Compound or Free Radical Compound The alkaline phosphatase-labelled antibody (IgG-ALP) prepared in Reference Example 2 was diluted with a Tris-HCl buffer (100 mM, pH 7.5; containing 0.1 mM zinc chloride) to 50 ng/ml, 100 ng/ml or 150 ng/ml.

A 5 mm wide and 30 mm long nitrocellulose membrane (produced by Millipore Corp.) was dotted with each of the labelled antibody solutions in a line 15 mm below the upper end by means of an applicator (Shot Master, produced by Musashi Engineering Co., Ltd.) and dried to adsorb and fix the labelled antibody. An absorbent pad and a substrate pad were fixed to the upper and lower ends of each membrane, respectively, in the same manner as in Example 1 to prepare three membranes different in labelled antibody concentration.

The substrate pad of each membrane was dotted with 5 μl of a 20 mg/ml BCIP solution and then with 5 μl of 100 mM EDTA-Cu, 50 mM EDTA-Fe, 100 mM EDTA-Zn or 100 mM N-oxyl-4-oxo-2,2,6,6-tetramethylpiperidine (AAQ-2, produced by Dojindo Laboratories) and dried at 37° C. for 10 minutes to prepare a test strip. The substrate was spread by dropping 200 μl of a CHES buffer (100 mM, pH 10.5; containing 1 mM magnesium chloride) to the substrate pad, and the time required for confirming color development with the naked eye was recorded. For control, the same test was carried out using a test strip having neither a chelate compound nor a free radical compound in the substrate pad. The results obtained are shown in Table 2 below.

TABLE 2

| Chelate Compound or Free Radical Compound | Average Detecting Time (sec) | | |
|---|---|---|---|
| | IgG-ALP Concentration (ng/ml) | | |
| | 50 | 100 | 150 |
| EDTA-Cu | 289 | 201 | 135 |
| EDTA-Fe | 260 | 187 | 110 |
| EDTA-Zn | 305 | 221 | 145 |
| AAQ-2 | 210 | 135 | 76 |
| Control | 360 | 305 | 280 |

EXAMPLE 4

Measurement of Color Developing Time with EDTA-Fe Added

Five test strips having applied thereto 150 ng/ml of an alkaline phosphatase-labelled antibody were prepared in the same manner as in Example 3. The substrate pad of all the test strips was dotted with a 20 mg/ml BCIP solution. The substrate pad of 5 test strips was further dotted with 2 μl or 5 μl of 10 mM EDTA-Fe or 1 μl, 2 μl or 5 μl of 100 mM EDTA-Fe and dried at 37° C. for 10 minutes. To the substrate pad was dropped 200 μl of a 100 mM CHES buffer (pH 10.5; containing 1 mM magnesium chloride) to develop the substrate. The time required for confirming color development with the naked eye was recorded. The results obtained are shown in Table 3 below.

TABLE 3

| Chelate Compound | Amount Added (μl) | Time of Detection (sec) | | |
|---|---|---|---|---|
| | | 1st Run | 2nd Run | Average |
| EDTA-Fe (10 mM) | 2 | 130 | 140 | 135 |
| | 5 | 100 | 110 | 105 |
| EDTA-Fe | 1 | 110 | 120 | 115 |

TABLE 3-continued

| Chelate Compound | Amount Added (μl) | Time of Detection (sec) | | |
|---|---|---|---|---|
| | | 1st Run | 2nd Run | Average |
| (100 mM) | 2 | 100 | 100 | 100 |
| | 5 | 110 | 100 | 105 |

EXAMPLE 5

Preparation of Test Strip for Assaying HBs Antigen

An anti-HBs antibody (2.86 μg) displaced with a phosphate buffer was applied in a dot to a 5 mm wide and 50 mm long nitrocellulose membrane (Hi-Flow Membrane, produced by Millipore Corp.) 15 mm below the upper end and dried. A labelled substance pad and a substrate pad were dotted with 0.16 μg of an alkaline phosphatase-labelled anti-HBs antibody (produced by Scantibodies; average molecular weight: 350,000) displaced with a phosphate buffer and 0.125 mg of BCIP (produced by Boehringer Mannheim Biochemica), respectively, followed by drying. A 100 mM CHES buffer (pH 10.5; containing 1 mM magnesium chloride) was used as a developing solution, to which 500 mM AAQ-2 (produced by Dojindo Laboratories) was added to a final concentration of 5 mM. The membrane, the substrate pad, the labelled substance pad, and an absorbent pad were disposed in a plastic case having a pot for the developing solution, a window for dropping a sample, and a window for detection to prepare a test strip for assaying an HBs antigen.

For control, a test strip was prepared in the same manner except for using a 100 mM CHES buffer (pH 10.5; containing 1 mM magnesium chloride) containing no AAQ-2 as a developing solution.

EXAMPLE 6

Assay of HBs Antigen

An HBs antigen was assayed by using the test strips prepared in Example 5. A serum sample (25 μl) containing an HBs antigen in a varied concentration (18.5 U/ml, 8.5 U/ml, 4.2 U/ml, 2.2 U/ml or 1.1 U/ml) was dropped on the specimen dotting zone. Immediately thereafter, the pot of the developing solution was pressed to spread the developing solution through the membrane, and the time for detecting positivity was measured. Three measurements were made for each sample to obtain an average time of detection. The results obtained are shown in Table 4.

EXAMPLE 7

Preparation of Test Strip for Assaying Anti-HBs Antibody

A 5 mm wide and 50 mm long cellulose membrane (produced by Millipore Corp.) was dotted 15 mm below the upper end with 0.7 μg of an HBs antigen (produced by Meiji Milk Products Co., Ltd.) displaced with a phosphate buffer and dried. An HBs antigen and alkaline phosphatase were linked by a maleimide-hinge method (see Ishikawa Eiji, Koso Hyoshikiho, p. 1, Gakkai Shuppan Center) to obtain an alkaline phosphatase-labelled HBs antigen (average molecular weight: about 3,000,000). The labelled antigen was displaced with a phosphate buffer and 0.025 μg was dotted to a labelled substance pad and dried. A substrate pad was spotted with 0.1 mg of BCIP and dried. A Good's buffer was used as a developing solution, to which 500 mM AAQ-2 (produced by Dojindo Laboratories) was added to a final concentration of 5 mM. The membrane, the substrate pad, the labelled substance pad, and an absorbent pad were placed in the same plastic case as used in Example 5 to prepare a test strip for assaying an anti-HBs antibody.

For control, a test strip was prepared in the same manner as described above, except for using an AAQ-2-free 100 mM CHES buffer (pH 10.5; containing 1 mM magnesium chloride) was used as a developing solution.

EXAMPLE 8

Assay of Anti-HBs Antibody

The test strips prepared in Example 7 were used. A serum sample (25 μl) containing an anti-HBs antibody in a varied concentration (30 mU/ml, 19.0 mU/ml, 9.6 mU/ml, 5.0 mU/ml, 2.5 mU/ml or 1.2 mU/ml) was dropped on the specimen dotting zone. Immediately thereafter, the pot of the developing solution was pressed to spread the developing solution through the membrane, and the time for detecting positivity was measured. Three measurements were made for each sample to obtain an average time of detection. The results obtained are shown in Table 5 below.

TABLE 4

| | Detecting Time (sec) | | | | | | | | | |
|---|---|---|---|---|---|---|---|---|---|---|
| | Concentration of HBs Antigen (U/ml) | | | | | | | | | |
| Radical | 18.5 | | 8.5 | | 4.2 | | 2.2 | | 1.1 | |
| Compound | AAQ-2 | control | AAQ-2 | control | AAQ-2 | control | AAQ-2 | control | AAQ-2 | control |
| 1st Run | 650 | 650 | 689 | 709 | 835 | 907 | 923 | 1140 | — | — |
| 2nd Run | 611 | 695 | 650 | 712 | 830 | 877 | 876 | 1100 | — | — |
| 3rd Run | 618 | 720 | 665 | 700 | 806 | 926 | 906 | 1165 | — | — |
| Average | 626 | 688 | 668 | 707 | 824 | 903 | 902 | 1135 | — | — |

—: Not detected.

TABLE 5

| | Detecting Time (sec) | | | | | | | | | | | |
|---|---|---|---|---|---|---|---|---|---|---|---|---|
| | Concentration of Anti-HBs Antibody (mU/ml) | | | | | | | | | | | |
| Radical | 30 | | 19 | | 9.6 | | 5.0 | | 2.5 | | 1.2 | |
| Compound | AAQ-2 | control | AAQ-2 | control | AAQ-2 | control | AAQ-2 | control | AAQ-2 | control | AAQ-2 | control |
| 1st Run | 595 | 720 | 660 | 795 | 756 | 870 | 848 | 1040 | 1321 | — | — | — |
| 2nd Run | 590 | 730 | 670 | 790 | 760 | 893 | 859 | 1043 | 1325 | — | — | — |
| 3rd Run | 592 | 730 | 665 | 793 | 760 | 870 | 880 | 1071 | 1420 | — | — | — |
| Average | 592 | 727 | 665 | 793 | 759 | 878 | 862 | 1051 | 1355 | — | — | — |

—: Not detected.

EXAMPLE 9

Measurement of Color Intensity at Various AAQ-2 Concn

A 5 mm wide and 50 mm long nitrocellulose membrane (produced by Millipore Corp) was dotted 15 mm below the upper end with 80 ng of an alkaline phosphatase-labelled antibody (average molecular weight: 300,000) and dried. A 100 mM CHES-NaOH buffer (containing 0.1 mM magnesium chloride) containing AAQ-2 in a varied concentration (1.25 mM, 2.5 mM, 5 mM, 10 mM or 20 mM) was used as a developing solution. A substrate pad was dotted with 0.1 mg of BCIP and dried. The developer pot was pressed to spread the developing solution. After 15 minutes' reacting, the intensity of the color developed on the dot of the enzyme-labelled antibody was measured with a color difference meter (manufactured by Minolta). For comparison, the same test was carried out by using a AAQ-2-free developing solution. The results obtained are shown in FIG. 1.

The indigoid dye forming reaction of an indolyl derivative with an enzyme can be accelerated by the presence of a free radical compound and/or a chelate compound thereby reducing the time required for detection. Therefore, EIA utilizing the color development system of the present invention achieves shortening of the assaying time and also makes it possible to detect a trace substance with high sensitivity.

While the invention has been described in detail and with reference to specific embodiments thereof, it will be apparent to one skilled in the art that various changes and modifications can be made therein without departing from the spirit and scope thereof.

What is claimed is:
1. An enzymatic color developing method comprising reacting an indolyl derivative represented by formula (I):

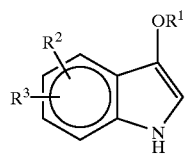

(I)

wherein $R^1$ represents an enzymatically releasable group; and $R^2$ and $R^3$ represents a hydrogen atom or a halogen atom, and an enzyme that can release group $R^1$, wherein said reacting is carried out in the presence of a free radical compound represented by formula (II):

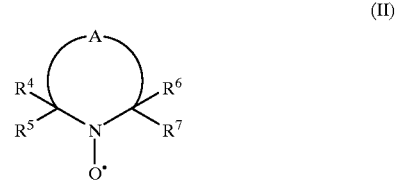

(II)

wherein A represents a substituted or unsubstituted methylene chain having 2 or 3 carbon atoms which may contain in its chain an oxygen atom or a carbonyl group; and $R^4$, $R^5$, $R^6$, and $R^7$ each represent a hydrogen atom or an alkyl group having 1 to 3 carbon atoms, and/or a chelate compound formed between a diamine derivative represented by formula (III):

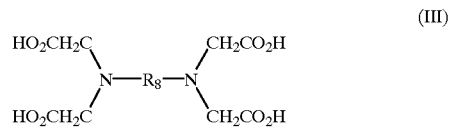

(III)

wherein $R^8$ represents an ethylene group or a cyclohexane-1,2-diyl group,
and a metal selected from the group consisting of iron, copper, zinc, cobalt, titanium, neodymium, manganese and europium.

2. The color developing method according to claim 1, wherein $R^4$, $R^5$, $R^6$, and $R^7$ each represents an alkyl group having 1 to 3 carbon atoms.

3. The color developing method according to claim 1, wherein the substituent on the substituted methylene chain having 2 or 3 carbon atoms is selected from the group consisting of a hydroxyl group, a carboxyl group, a carbamoyl group, and an amino group.

4. The color developing method according to claim 1, wherein said diamine derivative is ethylenediaminetetraacetic acid or trans-1,2-diaminecyclohexane-N,N,N',N'-tetraacetic acid.

5. The color developing method according to claim 1, wherein said enzyme is a phosphatase, and $R^1$ is a —$PO_3^{2-} \cdot 2M^+$ group, wherein M is a hydrogen atom, an alkali metal or toluidine.

6. The color developing method according to claim 1, wherein said enzyme is β-D-galactosidase, and $R^1$ is a β-D-galactopycanosyl group.

7. The color developing method according to claim 1, wherein said enzyme is β-D-glucosidase, and $R^1$ is a β-D-glucopyranosyl group.

* * * * *